US008461357B2

(12) United States Patent
Fairweather et al.

(10) Patent No.: US 8,461,357 B2
(45) Date of Patent: Jun. 11, 2013

(54) EXPEDITIOUS SYNTHESIS OF GIBBERELLIN A$_5$ AND ESTERS THEREOF

(75) Inventors: Kelly A. Fairweather, Calgary (CA); Lewis N. Mander, Calgary (CA); Richard P. Pharis, Cochrane (CA)

(73) Assignee: UTI Limited Partnership, Calgary, Alberta (CA)

( * ) Notice: Subject to any disclaimer, the term of this patent is extended or adjusted under 35 U.S.C. 154(b) by 35 days.

(21) Appl. No.: 13/119,889

(22) PCT Filed: Sep. 18, 2009

(86) PCT No.: PCT/IB2009/007067
§ 371 (c)(1),
(2), (4) Date: Jul. 12, 2011

(87) PCT Pub. No.: WO2010/032136
PCT Pub. Date: Mar. 25, 2010

(65) Prior Publication Data
US 2011/0263876 A1 Oct. 27, 2011

Related U.S. Application Data

(60) Provisional application No. 61/098,444, filed on Sep. 19, 2008.

(51) Int. Cl.
*C07D 307/77* (2006.01)
(52) U.S. Cl.
USPC .......................................................... 549/297
(58) Field of Classification Search
USPC .......................................................... 549/297
See application file for complete search history.

(56) References Cited

U.S. PATENT DOCUMENTS

| 4,243,594 A | 1/1981 | Beale et al. | 549/297 |
| 4,532,334 A | 7/1985 | Turner et al. | 549/297 |
| 5,767,042 A | 6/1998 | Pharis et al. | 504/297 |
| 7,199,082 B1 | 4/2007 | Chapman et al. | 504/115 |

FOREIGN PATENT DOCUMENTS

| DE | 102005018025 | 11/2006 |
| GB | 892777 | 3/1962 |
| WO | WO 96/06090 | 2/1996 |
| WO | WO 98/00375 | 1/1998 |

OTHER PUBLICATIONS

Longbottom et al. Tetrahedron 59 (2003) 6955-6966.*
"Gibberellin," *Wikipedia, The Free Encyclopedia*. Wikimedia Foundation, Inc., Jan. 28, 2008, accessed on Mar. 5, 2008.
"Organic Synthesis Group," accessed from http://rsc.anu.edu.au/~mander/, on Mar. 5, 2008.
Abstract of Carboni et al., "Estrogens III," *Gazzetta Chimica Italian*, 89:1717-1724, 1961.
Abstract of Duri et al., "Preparation of gibberellins A$_9$ and A$_{20}$ from gibberellic acid," *J Chem. Soc. Perkin Transactions: Organic and Bio-organic Chemistry*, 1:161-4, 1981.

Abstract of Hanson, "The partial synthesis and labeling of some gibberellins," *Mongraph—British Plant Growth Regulator Group*, 5:5-16, 1980.
Abstract of Jones et al., "Selective reduction of gibberellic acid," *J. Appl. Chem.*, 13(7): 324-328, 1963.
Abstract of MacMillian et al., "Plant hormones I. I Isolation of gibberllin A1 and gibberellin A5 from *Phaseolus multiflorus*," *Tetrahedron*, 11:60-66, 1960.
Abstract of: Fraga et al., "The stereochemistry of tri-n-butyltin hydride reductions in the preparation of ring a deoxygibberellins," *J Chem. Soc. Perkin Transactions: Organic and Bio-organic Chemistry*, (5): 1109-1113, 1984.
Bearder et al., "Allylic chlorination of gibberllins A$_3$ and A$_7$ methyl esters and of gibberllin A$_3$: preparation of gibberllin A$_5$," *J. of Chem. Soc. Perkin Transactions*, 672-678, 1981.
Ben-Tal, "Are gibberellins capable of replacing the environmental flowering signal?" *Israel J. of Plant Sciences*, 48:205-215, 2000.
Corey et al., "Stereospecific elaboration of the A ring of gibberellic acid by partial synthesis," *J. Am. Chem. Soc.*, 93:7316- 7317, 1971.
Grootaert and De Clercq, "A novel expeditious entry into gibberellins. The total synthesis of (±)-GA$_5$," *Tet. Lett.*, 27:1731-1734, 1986.
Hanson, Monograph-British Plant Growth Regulator Group, 5:5-16, 1980.
International Preliminary Report on Patentability issued in PCT/IB2009/007067, dated Mar. 22, 2011.
International Search Report issued in PCT/IB2009/007067, dated Feb. 12, 2010.
King and Evans, "Gibberellins and flowering of grasses and cereals: prizing open the lid of the "florigen" black box," *Annu. Rev. Plant Rev. Plant Biol.*, 54:307-328, 2006.
King and Evans, "Regulation of flowering in the long-day grass *Lolium temulentum* by gibberellins and the Flowering Locus T gene," *Plant Physiol.*, 141: (2):498-507, 2006.
Longbottom et al., "Total Synthesis of Polycephalin C and Determination of the Absolute Configurations at the 3",4" Ring Junction," *Agnew. Chemie, Int'l Ed.*, 41:2786-2790, 2002.
Longbottom et al., "Total synthesis of the polyenoyltetramic acid polycephalin C," *Tetrahedron*, 59:6955-6966, 2003.
MacMillian et al., "Plant hormones—I: Isolation of gibberellin A$_1$ and gibberellins A$_5$ from *Phaseolus multiflorus*," *Tetrahedron*, 11:60-66, 1960.
Murofushi et al., "Preparation of radioactive gibberllins A$_{20}$, A$_5$, A$_8$," *Agric. Biol. Chem.*, 41(6): 1075-1079, 1977.
Musgrave et al., "Radioactive gibberellin A$_5$ and its metabolism in dwarf peas," *Plant Physiol.*, 45:56-61, 1970.
Myers and Zheng, "An efficient method for the reductive transposition of allylic alcohols," *Tetrahedron Letters*, 37:(28): 4841-4844, 1966.

(Continued)

*Primary Examiner* — Nizal Chandrakumar
(74) *Attorney, Agent, or Firm* — Gowling Lafleur Henderson

(57) ABSTRACT

An expeditious synthesis of gibberellin A$_5$ (GA$_5$) esters is presented, from which GA$_5$ may be prepared. The synthesis offers an inexpensive route of few steps to these compounds, starting from gibberellin A$_3$ (GA$_3$) esters in the presence of a metal hydride.

35 Claims, No Drawings

OTHER PUBLICATIONS

Nuyttens et al., "The intramolecular diels-alder reaction with furandiene: a novel route to (±)-gibberellin $A_5$," *Synlett*, 7:526-528, 1991.

Office Communication issued in corresponding New Zealand Patent Application No. 591796, dated Jul. 28, 2011.

Pharis, "Flowering of Chrysanthemum under non-inductive long days by gibberellins and N6-benzyladenine," *Planta Berl.*, 105:205-212, 1972.

Shimano et al., "Synthesis of gibberellin $A_1$, $A_5$, $A_{55}$ and $A_{60}$, metal-ammonia reduction of gibberellic acid and its derivative," *Chem. Pharm. Bull*, 38:276-278, 1990.

Yokota and Takahashi, "Gibberellin A59: A New Gibberellin from *Canavalia gladiata*," *Agric. Biol. Chem.*, 45(5):1251-1254, 1981.

\* cited by examiner

EXPEDITIOUS SYNTHESIS OF GIBBERELLIN A₅ AND ESTERS THEREOF

This application is a national phase application under 35 U.S.C. §371 of International Application No. PCT/IB2009/007067 filed Sep. 18, 2009, which claims the benefit of U.S. Provisional Application Serial No. 61/098,444 filed Sep. 19, 2008, the entire text of each of the above-referenced disclosures is specifically incorporated herein by reference without disclaimer.

BACKGROUND OF THE INVENTION

1. Field of the Invention

The present invention relates generally to synthetic organic chemistry and plant growth hormones. More particularly, it concerns the efficient preparation of gibberellin $A_5$ in a cost-effective manner.

2. Description of the Related Art

There are six major groups of plant hormones: auxins, gibberellins, ethylene, cytokinins, brassinosteroids and abscisic acid. The more commonly used groups in agriculture, floriculture, forestry and horticulture are the auxins, gibberellins, ethylene and cytokinins. Gibberellins are a group of tetracyclic diterpenoid compounds, and the skeleton below shows the carbon numbering of the $C_{19}$ class of gibberellins:

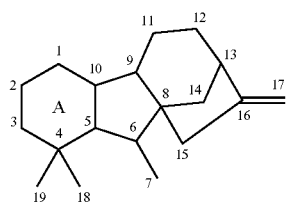

Many gibberellins occur naturally in plants and some of these gibberellins can be produced by fermentation methods. There are over 130 gibberellins discussed in the literature. Individual gibberellins are designated with an integer that reflects the chronological order of discovery. Four examples of gibberellins that occur naturally in higher plants are shown below and three of these (gibberellins $A_3$, $A_4$ and $A_7$) can also be produced in commercial quantities by fungal fermentation.

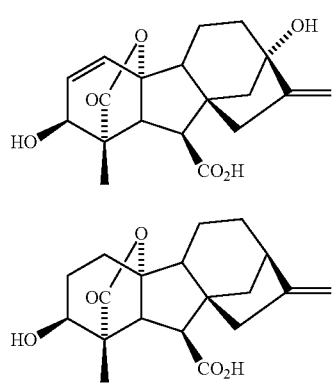

-continued

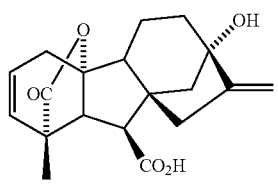

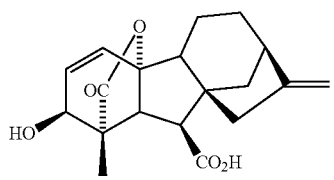

Naturally occurring gibberellins are used in all of the above-mentioned fields to, for example, promote flowering. Three gibberellins have been used extensively for commercial purposes: $GA_3$ (also known as gibberellic acid) and a mixture of $GA_4$ and $GA_7$ ($GA_{4/7}$). All three are native to higher plants and can be derived from fungal fermentations. However, when applied exogenously to higher plants they can often have detrimental side effects. For example, $GA_3$ often produces excessive stem elongation when applied to many plants, which can be undesirable in terms of lodging (falling over) in rain, or aesthetically when used for floriculture purposes. Like $GA_3$, $GA_{4/7}$ can also promote excessive (undesirable) stem elongation and both $GA_3$ and $GA_7$ can be excessively persistent when applied to higher plants due to the C-1,2 double bond in Ring A (shown above). Therefore, while applied gibberellins can promote flowering, there may also be the detrimental effect of increased shoot and stem growth (excessive elongation).

Preventing excessive shoot growth in a flowering plant is useful in many circumstances. For example, this effect makes the plant more resistant to falling over under adverse weather conditions such as wind, rain, hail and snow. This effect also makes the plant more compact, more stocky and more resistant to lodging as a result of weather conditions or as a result of heavy fruit or seed or grain production. In orchard situations, or in floriculture, for example, a more compact nature of a shrub or tree is valuable for a variety of reasons, including ease of tending the plant, picking the fruit, aesthetics, applying other treatments and reducing the necessity to prune the plant.

For the promotion of flowering and other benefits, the use of $GA_5$ offers advantages over the currently used $GA_3$. For example, $GA_5$ is an exceptionally florigenic molecule (King and Evans, 2003), but does not suffer the side effects of excessive shoot growth and flower stalk elongation to the degree seen with $GA_3$ and other gibberellins (King and Evans, 2003; Pharis, 1972; Ben-Tal, 2000). Moreover, the use of an inexpensively produced $GA_5$ preparation offers cost advantages over, for example, $GA_{4/7}$. $GA_5$ has been prepared by some groups; however the processes are frequently inefficient and the reagents quite expensive. Since it has been very expensive to synthesize, $GA_5$ is typically not used in agriculture or the other commercial areas mentioned above.

SUMMARY OF THE INVENTION

The synthetic methodology of the present invention provides inexpensive and facile access to $GA_5$ esters. Simple removal of the ester moiety by well-known techniques may then reveal GA$_5$. These methods allow production of GA$_5$ in a manner that facilitates its use in agriculture, floriculture, forestry and horticulture.

Accordingly, the present invention contemplates a method of preparing a compound of formula (I)

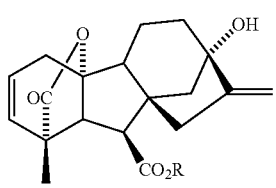

(I)

wherein R is alkyl$_{(C\leq 8)}$, alkenyl$_{(C\leq 8)}$, or aralkyl$_{(C\leq 8)}$, or a substituted version of any of these groups, comprising reacting a compound of formula (II)

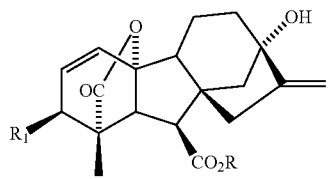

(II)

wherein R is as defined above, and R$_1$ is an alkyl$_{(C\leq 8)}$ sulfonate or an aryl$_{(C\leq 8)}$ sulfonate, or a substituted version of either of these groups, in the presence of a metal hydride to produce a mixture comprising the compound of formula (I). In certain embodiments, the compound of formula (I) is the predominant species in the mixture. By "predominant," it is meant that a specified compound is present in an amount that is higher than any other compound in the mixture. In certain embodiments, R$_1$ is not a mesylate.

The metal hydride that is employed in methods of the present invention may be any metal hydride known in the art, and such hydrides are commercially available. In certain embodiments, the metal hydride is NaBH$_4$ or LiAlH$_4$. The number of molar equivalents of metal hydride employed in methods of the present invention may range from about 1 to about 10, for example, including integers and non-integers. In certain embodiments, the number of equivalents may be about, at most about, or at least about 1, 1.5, 2, 2.5, 3, 3.5, 4, 4.5, 5, 5.5, 6, 6.5, 7, 7.5, 8, 8.5, 9, 9.5, 10, or higher, or any range derivable therein. In particular embodiments, the number of equivalents may range from about 2-5. In certain embodiments, the metal hydride is NaBH$_4$, and the number of equivalents of NaBH$_4$ ranges from about 2-5.

In certain embodiments of the present invention, the reaction of the compound of formula (II) as noted above is performed in the presence of a dipolar aprotic solvent. Dipolar aprotic solvents are well-known in the art and are commercially available. In certain embodiments, the dipolar aprotic solvent is further defined as DMF, DMSO or dimethyl acetamide. In particular embodiments, the dipolar aprotic solvent is DMF. In certain embodiments, ether-type solvents may be employed, which are also well-known and commercially available. Such solvents include THF and 1,2-dimethoxyethane. Combinations of solvents are also contemplated.

Methods of the present invention may further comprise obtaining a compound of formula (II). Compounds of formula (II) may be produced synthetically. For example, one may purchase GA$_3$ and then esterify it using, for example, an alkyl$_{(C\leq 8)}$ halide, an aryl$_{(C\leq 8)}$ halide, or an aralkyl$_{(C\leq 8)}$ halide, or a substituted version of any of these groups, to produce a compound of formula (III)

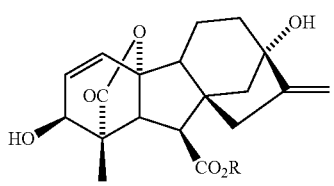

(III)

wherein R is alkyl$_{(C\leq 8)}$, alkenyl$_{(C\leq 8)}$, or aralkyl$_{(C\leq 8)}$, or a substituted version of any of these groups. As a next step, one may react the compound of formula (III) in the presence of a sulfonylating agent to produce a compound of formula (II). Sulfonylating agents are well-known in the art, and non-limiting examples include alkyl$_{(C\leq 8)}$ sulfonyl chlorides and aryl$_{(C\leq 8)}$ sulfonyl chlorides (e.g., tosyl chloride, benzenesulfonyl chloride and methane sulfonyl chloride).

In certain embodiments, methods of the present invention may further comprise isolating the compound of formula (I) from the mixture. Methods of isolation in this or any other method discussed herein are well-known in the art and include, for example, crystallization, silica gel column chromatography, and HPLC. In certain embodiments, isolation is performed using crystallization.

Methods of the present invention may also further comprise removing the R group of the compound of formula (I) to produce GA$_5$. Methods of removing the R group (that is, de-esterification) are well-known in the art and include basic hydrolysis, for example. Protocols for the removal of ester groups are described in Smith and March (2001), for example, which is incorporated by reference in its entirety. In certain embodiments, the removal is performed before isolation of the compound of formula (I) from the mixture. In other embodiments, the removal is performed after isolation of the compound of formula (I) from the mixture.

The mixture comprising the compound of formula (I) may further comprise a compound of formula (IV):

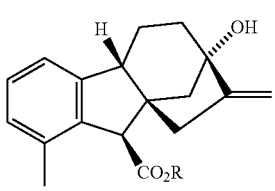

(IV)

wherein R is alkyl$_{(C\leq 8)}$, alkenyl$_{(C\leq 8)}$, or aralkyl$_{(C\leq 8)}$, or a substituted version of any of these groups. The ratio of the compound of formula (I) to the compound of formula (IV) may be greater than 1:1 in this mixture, in certain embodiments. In certain embodiments, the ratio of the compound of formula (I) to the compound of formula (IV) is greater than about 4:1. In certain embodiments, the ratio of the compound of formula (I) to the compound of formula (IV) is greater than about 7:1. In certain embodiments, the ratio of the compound of formula (I) to the compound of formula (IV) is greater than about 10:1. In certain embodiments, the ratio of the compound of formula (I) to the compound of formula (IV) is greater than about 15:1. In certain embodiments, the ratio of the compound of formula (I) to the compound of formula (IV) is about 20:1. In certain embodiments, the ratio of the compound of formula (I) to the compound of formula (IV) is greater than about 20:1.

Also contemplated by the present invention are methods of preparing GA$_5$ comprising (a) reacting a compound of formula (II)

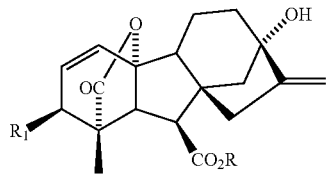

wherein R is alkyl$_{(C \leq 8)}$, alkenyl$_{(C \leq 8)}$, or aralkyl$_{(C \leq 8)}$, or a substituted version of any of these groups, and R$_1$ is an alkyl$_{(C \leq 8)}$ sulfonate or an aryl$_{(C \leq 8)}$ sulfonate, or a substituted version of either of these groups, in the presence of a metal hydride and a dipolar aprotic solvent to produce a mixture comprising a compound of formula (I)

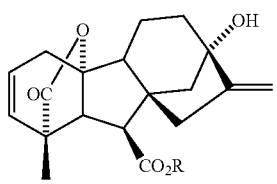

wherein R is alkyl$_{(C \leq 8)}$, alkenyl$_{(C \leq 8)}$, or aralkyl$_{(C \leq 8)}$, or a substituted version of any of these groups, and (b) removing the R group of the compound of formula (I) to produce GA$_5$.

As noted above, the metal hydride may be any metal hydride known in the art, including, for example, NaBH$_4$ or LiAlH$_4$. Also as noted above, the dipolar aprotic solvent employed may be any such solvent known in the art, including, for example, DMF, DMSO, dimethyl acetamide, or ether-based solvents.

Such methods may further comprise obtaining the compound of formula (II), as described above. In certain embodiments, such methods may further comprise isolating the compound of formula (I) from the mixture of step (a). Such isolation methods are described above. Regarding step (b), the removal of the R group (de-esterification) may be performed as described herein. The removal of the R group may be performed either before or after isolation of the compound of formula (I). Moreover, the number of molar equivalents of metal hydride may equal any amount discussed herein, such as about 1 to about 10. Regarding step (a) above or any other embodiment regarding a mixture that comprises a compound of formula (I), the compound of formula (I) may be the predominant species in the mixture. The mixture may further comprise a compound of formula (IV)

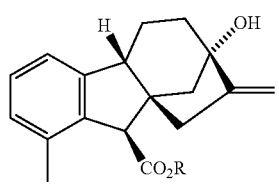

wherein R is alkyl$_{(C \leq 8)}$, alkenyl$_{(C \leq 8)}$, or aralkyl$_{(C \leq 8)}$, or a substituted version of any of these groups. The ratio of the compound of formula (I) to the compound of formula (IV) may be greater than 1:1 in such a mixture, in certain embodiments. Indeed, the ratios may be any ratio discussed herein regarding compounds of formulas (I) and (IV), such as about 1:1 to about 20:1, or higher.

In any embodiment herein, R may be further defined as alkyl$_{(C \leq 8)}$, such as methyl, ethyl, n-propyl, or isopropyl. R may be an alkenyl$_{(C \leq 8)}$ group, such as allyl. R may be a substituted or unsubstituted aralkyl$_{(C \leq 8)}$ group, such as benzyl or 2-furanylmethyl. In any embodiment herein, R$_1$ may be further defined as an aryl$_{(C \leq 8)}$ sulfonate, such as a tosylate.

In any embodiment herein regarding alkyl$_{(C \leq 8)}$, aryl$_{(C \leq 8)}$ and aralkyl$_{(C \leq 8)}$ groups (e.g., alkyl$_{(C \leq 8)}$, alkyl$_{(C \leq 8)}$ sulfonate, alkyl$_{(C \leq 8)}$ halide, aryl$_{(C \leq 8)}$ sulfonate, aralkyl$_{(C \leq 8)}$, etc.), it is specifically contemplated that the number of carbons may be 1, 2, 3, 4, 5, 6, 7, or 8, or any range derivable therein. It is also specifically contemplated that any particular number of carbon atoms may be excluded from any of these definitions.

As used herein, "halide" means independently —F, —Cl, —Br or —I and "sulfonyl" means —SO$_2$—.

The term "alkyl," when used without the "substituted" modifier, refers to a non-aromatic monovalent group, having a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$) CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group, having a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O) OH, —CH$_2$C(O)OCH$_3$, —CH$_2$C(O)NH$_2$, —CH$_2$C(O) NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N (CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$. In certain embodiments, "lower alkyl" groups are contemplated, wherein the total number of carbon atoms in the lower alkyl group is 6 or less.

The term "alkenyl" when used without the "substituted" modifier refers to a monovalent group, having a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "substituted alkenyl" refers to a monovalent group, having a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH=CHF, —CH=CHCl and —CH=CHBr, are non-limiting examples of substituted alkenyl groups.

The term "aryl," when used without the "substituted" modifier, refers to a monovalent group, having an aromatic carbon atom as the point of attachment, said carbon atom forming part of a six-membered aromatic ring structure wherein the ring atoms are all carbon, and wherein the monovalent group consists of no atoms other than carbon and hydrogen. Non-limiting examples of aryl groups include phenyl (Ph), methylphenyl, (dimethyl)phenyl, —C$_6$H$_4$—CH$_2$CH$_3$ (ethylphenyl), —C$_6$H$_4$—CH$_2$CH$_2$CH$_3$ (propylphenyl), —C$_6$H$_4$—CH(CH$_3$)$_2$, —C$_6$H$_4$—CH(CH$_2$)$_2$, —C$_6$H$_3$(CH$_3$)CH$_2$CH$_3$ (methylethylphenyl), —C$_6$H$_4$—CH=CH$_2$ (vinylphenyl), —C$_6$H$_4$—CH=CHCH$_3$, —C$_6$H$_4$CCH, —C$_6$H$_4$C≡CCH$_3$, naphthyl, and the monovalent group derived from biphenyl. The term "substituted aryl" refers to a monovalent group, having an aromatic carbon atom as the point of attachment, said carbon atom forming part of a six-membered aromatic ring structure wherein the ring atoms are all carbon, and wherein the monovalent group further has at least one atom independently selected from the group consisting of N, O, F, Cl, Br, I, Si, P, and S, Non-limiting examples of substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$C(O)CH$_3$, —C$_6$H$_4$NH$_2$, —C$_6$H$_4$NHCH$_3$, —C$_6$H$_4$N(CH$_3$)$_2$, —C$_6$H$_4$—CH$_2$OH, —C$_6$H$_4$—CH$_2$OC(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, and —C$_6$H$_4$CON(CH$_3$)$_2$.

The term "aralkyl" when used without the "substituted" modifier refers to the monovalent group-alkanediyl-aryl, in which the terms alkanediyl and aryl are each used in a manner consistent with the definitions provided herein. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are (3-chlorophenyl)-methyl, 2-oxo-2-phenyl-ethyl (phenylcarbonylmethyl), 2-chloro-2-phenyl-ethyl and 2-methylfuranyl.

The term "alkynediyl" when used without the "substituted" modifier refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and no atoms other than carbon and hydrogen. The groups, —C≡C—, —C≡CCH$_2$—, and —C≡CCH(CH$_3$)— are non-limiting examples of alkynediyl groups. The term "substituted alkynediyl" refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and at least one atom independently selected from the group consisting of N, O, F, Cl, Br, I, Si, P, and S. The groups —C≡CCH(F)— and —C≡CCH(Cl)— are non-limiting examples of substituted alkynediyl groups.

The terms "alkyl sulfonate" and "aryl sulfonate" refer to compounds having the structure —OSO$_2$R, wherein R is alkyl or aryl, as defined above, including substituted versions thereof. Non-limiting examples of alkyl sulfonates and aryl sulfonates include mesylate, triflate, tosylate and besylate. In certain embodiments, mesylates are excluded from compounds of the present invention.

As used herein, "protecting group" refers to a moiety attached to a functional group to prevent an otherwise unwanted reaction of that functional group. The term "functional group" generally refers to how persons of skill in the art classify chemically reactive groups. Examples of functional groups include hydroxyl, amine, sulfhydryl, amide, carboxylic acid, ester, carbonyl, etc. Protecting groups are well-known to those of skill in the art. Non-limiting exemplary protecting groups fall into categories such as hydroxy protecting groups, amino protecting groups, sulfhydryl protecting groups and carbonyl protecting groups. Such protecting groups, including examples of their installation and removal, may be found in Greene and Wuts (1999), incorporated herein by reference in its entirety. The starting materials, products and intermediates described herein are also contemplated as protected by one or more protecting groups—that is, the present invention contemplates such compounds in their "protected form," wherein at least one functional group is protected by a protecting group.

Compounds of the present invention may contain one or more asymmetric centers and thus can occur as racemates and racemic mixtures, single enantiomers, diastereomeric mixtures and individual diastereomers. In certain embodiments, a single diastereomer is present. All possible stereoisomers of the compounds of the present invention are contemplated as being within the scope of the present invention. However, in certain aspects, particular diastereomers are contemplated. The chiral centers of the compounds of the present invention can have the S- or the R-configuration, as defined by the IUPAC 1974 Recommendations. Thus, in certain aspects, compounds of the present invention may comprise S- or R-configurations at particular carbon centers.

Persons of ordinary skill in the art will be familiar with methods of purifying compounds of the present invention. One of ordinary skill in the art will understand that compounds of the present invention can generally be purified at any step, including the purification of intermediates as well as purification of the final products. Purification procedures include, for example, silica gel column chromatography, HPLC, or crystallization. In particular embodiments, trituration is employed. In certain embodiments, solvent extraction is employed.

Modifications or derivatives of the compounds disclosed throughout this specification are contemplated as being useful with the methods and compositions of the present invention. Derivatives may be prepared and the properties of such derivatives may be assayed for their desired properties by any method known to those of skill in the art. A non-limiting example of a method for testing GA$_5$ derivatives as compared to GA$_5$ is described by Ben-Tal (2000), which is incorporated herein by reference in its entirety.

In certain aspects, "derivative" refers to a chemically-modified compound that still retains the desired effects of the compound prior to the chemical modification. Using GA$_5$ as an example, a "GA$_5$ derivative" refers to a chemically modified $GA_5$ that still retains the desired effects of the parent $GA_5$ prior to its chemical modification. Such effects may be enhanced (e.g., slightly more effective, twice as effective, etc.) or diminished (e.g., slightly less effective, 2-fold less effective, etc.) relative to the parent $GA_5$, but may still be considered a $GA_5$ derivative. Such derivatives may have the addition, removal, or substitution of one or more chemical moieties on the parent molecule. Non-limiting examples of the types of modifications that can be made to the compounds and structures disclosed herein include the addition or removal of lower unsubstituted alkyls such as methyl, ethyl, propyl, or substituted lower alkyls such as hydroxymethyl or aminomethyl groups; carboxyl groups and carbonyl groups; hydroxyls; nitro, amino, amide, imide, and azo groups; sulfate, sulfonate, sulfono, sulfhydryl, sulfenyl, sulfonyl, sulfoxido, sulfonamide, phosphate, phosphono, phosphoryl groups, and halide substituents. Additional modifications can include an addition or a deletion of one or more atoms of the atomic framework, for example, substitution of an ethyl by a propyl, or substitution of a phenyl by a larger or smaller aromatic group. Alternatively, in a cyclic or bicyclic structure, heteroatoms such as N, S, or O can be substituted into the structure instead of a carbon atom.

Salts of any of the compounds of the present invention are also contemplated. The term "salt(s)" as used herein, is understood as being acidic and/or basic salts formed with inorganic and/or organic acids and bases. Zwitterions (internal or inner salts) are understood as being included within the term "salt(s)" as used herein, as are quaternary ammonium salts, such as alkylammonium salts. Salts include, but are not limited to, sodium, lithium, potassium, amines, tartrates, citrates, hydrohalides and phosphates.

Hydrates of compounds of the present invention are also contemplated. The term "hydrate" when used as a modifier to a compound means that the compound has less than one (e.g., hemihydrate), one (e.g., monohydrate), or more than one (e.g., dihydrate) water molecules associated with each compound, such as in solid forms of the compound.

It is contemplated that any embodiment discussed in this specification can be implemented with respect to any method, compound, or composition of the invention, and vice versa. Furthermore, compounds and compositions of the invention can be used to achieve methods of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value. In any embodiment discussed in the context of a numerical value used in conjunction with the term "about," it is specifically contemplated that the term about can be omitted.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE ILLUSTRATIVE EMBODIMENTS

I. Gibberellin $A_5$

The naturally occurring plant product $GA_5$ may be obtained using both non-synthetic and synthetic means. $GA_5$ has been isolated from seeds (MacMillan et al., 1961; MacMillan et al., 1959) and has been reported to be produced by bacteria in a mixture with other gibberellins (Joo et al., 2004), although its presence in the medium used to ferment the bacteria cannot be excluded. Synthetic methods of preparing $GA_5$, radioactive $GA_5$, and $GA_5$ methyl ester have been discussed in the literature. See, e.g., Nuyttens et al., 1991; Shimano et al., 1990; Grootaert and De Clercq, 1986; Bearder et al., 1981; Hanson, 1980; Murofushi et al., 1977; Duri et al., 1981; Great Britain Patent 892777; and U.S. Pat. No. 5,767, 042. Many of these reactions require expensive reagents, entail multiple steps, or are impractical for large-scale production.

By contrast, the preparation of $GA_5$ and various esters from a $GA_3$ ester as provided by the present invention offers an inexpensive and efficient means of accessing these compounds. As a starting material, $GA_3$ is readily available at low cost, and the reagents employed to produce $GA_5$ esters and $GA_5$ as described herein are typically cheaper than those found in other preparations. Moreover, relatively inexpensive and simple triturations purify the sulfonylated $GA_3$ ester intermediate and $GA_5$ ester product. Optional removal of the $GA_5$ ester reveals $GA_5$.

In keeping with the description above, $GA_5$ as produced herein may be used in agriculture, floriculture, forestry and horticulture. For example, $GA_5$ may be used to stimulate flowering, such as in grasses, grains and canola. Cytokinins, auxins, brassinosteroids, or other plant growth regulators (natural or synthetic) may be combined with $GA_5$ for flowering and/or growth purposes, such as for canola. Other uses include stimulation of a more uniform bud break in woody angiosperm fruit trees (e.g., peach and apricot) as well as promotion of flowering in a variety of biennial bearing plants, such as apples, apricots, pecan and coffee plants. $GA_5$ may be employed in outdoor conditions that are less than favorable for flowering and shoot growth, such as lower-than-average temperatures, to achieve the benefits discussed herein.

In addition, the products and intermediates produced using methods of the present ention may also be employed as materials to generate $GA_5$ derivatives as well as other known gibberellins and derivatives thereof. Furthermore, radioactive isotopes and or stable isotopes may be incorporated during the syntheses described herein such that the labelled products may be used to monitor these compounds in plant studies.

II. Application of $GA_5$

Gibberellin $A_5$ may be provided to the commercial user as the crystalline parent material (with directions for solubilization using an appropriate solvent, such as ethanol or water), or as a salt, e.g., potassium salt, or as a formulated material (concentrate) that is relatively stable over time and can be easily diluted according to directions for practical use as a spray, either to drip off (1 to 300 ppm) or at recommended doses per acre or per hectare in a given volume of solution, e.g., 0.1, 0.3, 1, 3, 10, 33 etc., grams per 100 litres applied to each hectare.

Frequency of application may be once, or more than once, such as twice, thrice, etc., where repeated applications may be necessary, or may be used in lieu of a single high dose application. Appropriate surfactants (to lower surface tension of the application solution) may be included in the formulated concentrate. $GA_5$ or one of its derivatives may also be formulated according to protocols provided by European Patent 1 094 708, incorporated herein by reference.

Application may take place at or prior to the time at which each individual plant species is known to "make the decision" to induce potential floral buds (meristems) to begin the path toward floral bud differentiation and development. This could be early spring for certain species of annuals, biennials, or perennials, or in the previous late summer autumn/early winter for some biennials, or in the previous summer/autumn for some perennials, including woody plants (Pharis and King, 1985).

III. EXAMPLES

The following examples are included to demonstrate particular embodiments of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Synthesis of $GA_3$ Methyl Ester Tosylate (ent-10β,13-Dihydroxy-3α-tosyloxy-20-norgibberella-1,16-diene-7,19-dioic acid 7-methyl Ester 19,10-lactone)

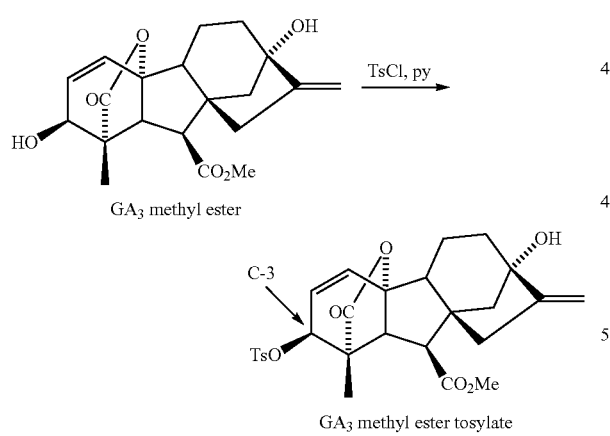

The starting $GA_3$ methyl ester was prepared by alkylating $GA_3$ (Zhejiang Shenghua Biok Biology Co., Ltd., China; imported by Bloomfresh, Pty Ltd, Cheltenham VIC., Australia) using methyl iodide and $K_2CO_3$. Toluenesulfonyl chloride (11.2 g, 58.9 mmol) was added to purified $GA_3$ methyl ester (10.6 g, 29.4 mmol) in pyridine (50 mL) at 0° C. under nitrogen. The reaction mixture was stirred for 24 h warming to 15° C., then quenched with water (50 mL) and diluted with dichloromethane (100 mL). The organic phase was separated and the aqueous phase extracted with dichloromethane (3×30 mL). The combined organic extracts were washed with 1 M HCl (20 mL), water (20 mL), brine (20 mL) then dried over magnesium sulfate. Concentration of the organic phase in vacuo gave a yellow solid which was purified by trituration with hexane to give the desired tosylate as a white solid (12.0 g, 80%).

Characterization of $GA_3$ methyl ester tosylate: m.p: 140-142° C.; IR (thin film) $cm^{-1}$: 3541s (C—OH), 2939 (C—H), 1778s (C=O), 1729s (C=O), 1454, 1360, 1175; 1H NMR (300 MHz, $CDCl_3$) δ: 0.95 (s, 3H, 18-$CH_3$), 1.63-2.22 (m, 10H), 2.46 (s, 3H, -Ts), 2.70 (ABd, J=10.8 Hz, 1H, H-6), 3.25 (ABd, J=10.8 Hz, 1H, H-5), 3.71 (s, 3H, —$CO_2Me$), 4.80 (d, J=3.6 Hz, 1H, H-3), 4.96 (s, 1H, H-17), 5.26 (s, 1H, H'-17), 5.80 (dd, J=9.3 Hz, 2.7 Hz, 1H, H-2), 6.38 (d, J=9.3 Hz, 1H, H-1), 7.36 (d, J=8.1 Hz, 2H, -Ts), 7.80 (d, J=8.1 Hz, 2H, -Ts); $^{13}C$ NMR (75 MHz, $CDCl_3$) δ: 14.5, 16.8, 21.7, 38.0, 42.9, 44.5, 50.1, 50.4, 50.6, 52.2, 52.6, 53.0, 77.0, 77.9, 90.0, 107.7, 127.9, 128.6, 130.0, 132.9, 135.2, 145.4, 156.5, 171.8, 176.3; LRMS (m/z): 514 ($M^+$, 2%), 454 (5%), 342 (15), 298 (51), 238 (100), 211 (49), 195 (58), 155 (61), 91 (62); HRMS: $C_{27}H_{30}O_8S$ ($M^+$) requires 514.1661, found 514.1655.

Example 2

Synthesis of $GA_5$ Methyl Ester (ent-10β,13-Dihydroxy-20-norgibberella-2,16-diene-7,19-dioic Acid 7-methyl Ester 19,10-lactone)

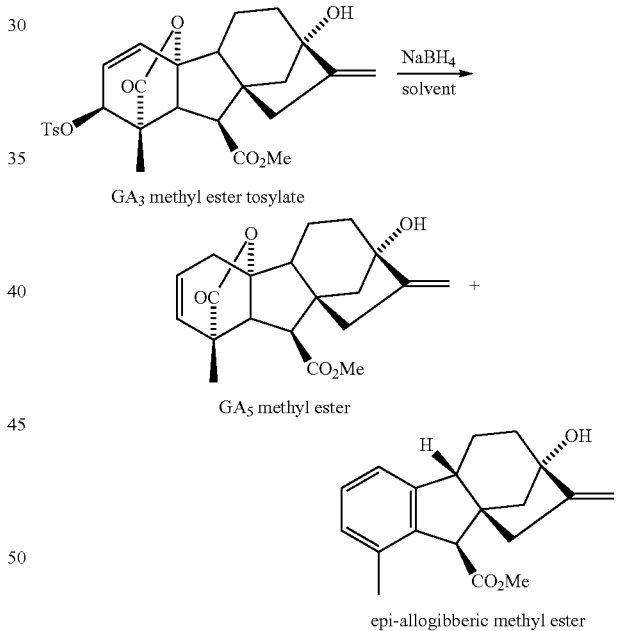

DMF (80 mL) was added to the tosylate from Example 1 (8.4 g, 16.3 mmol) and sodium borohydride (2.16 g, 57.2 mmol) at 0° C. under nitrogen. The mixture was warmed to room temperature and stirred for 18 h. The reaction was then quenched with water (50 mL) and diluted with ethyl acetate (50 mL). The organic phase was separated and the aqueous phase extracted with ethyl acetate (3×50 mL). The aqueous phase was then saturated with sodium chloride and further extracted with ethyl acetate (2×50 mL). The combined organic extracts were washed with water (50 mL), brine (50 mL), dried over magnesium sulfate and concentrated in vacuo to give a yellow wax. Purification by trituration with ether gave $GA_5$ methyl ester as a white solid (2.54 g, 45%). To establish the total amount of GA$_5$ methyl ester produced, the mother liquor was further purified by flash column chromatography using ethyl acetate:hexane (3:7) as eluant to give epi-allogibberic methyl ester as a white wax (0.67 g, 14%), and more GA$_5$ methyl ester (1.11 g, 20%). Thus, the total yield of GA$_5$ methyl ester obtained was 3.65 g, 65%.

This synthesis was carried out on 100 mg, 500 mg, and 10 g scales (all approx.). It is noted that cyanoborohydride did not produce favorable results, and that use of methanesulfonate did not work under these conditions. In each synthesis, the predominant product obtained was GA$_5$ methyl ester. However, this was unexpected, as hydride reductions of allylic sulfonates invariably afford mixtures of double bond isomers that strongly favor products in which the double bond does not migrate. (Longbottom et al., 2002; Longbottom et al., 2003). Under the reaction conditions described by this Example and elsewhere in this application, (1) the formation of a single alkene isomer is unprecedented, and (2) the favored formation of the S$_N$2' product (i.e., where the double bond has migrated) is again without precedent. The references cited above describe reductions that give ~85:15 alkene mixtures favoring S$_N$2 products (i.e., no migration of the double bond).

Characterization of GA$_5$ methyl ester: m.p: 179-189° C.; IR (thin film) cm$^{-1}$: 3479s (C—OH), 2932 (C—H), 1752s (C=O), 1732s (C=O), 1454, 1381, 1199; $^1$H NMR (300 MHz, CDCl$_3$) δ: 1.23 (s, 3H, 18-CH$_3$), 1.62-2.18 (m, 9H), 2.32 (m, 1H), 2.59 (m, 1H), 2.66 (ABd, J=9.6 Hz, 1H, H-6), 2.79 (ABd, J=9.6 Hz, 1H, H-5), 3.72 (s, 3H, —CO$_2$Me), 4.95 (s, 1H, H-17), 5.24 (s, 1H, H'-17), 5.67 (m, 1H, H-2), 5.80 (m, 1H, H-3); $^{13}$C NMR (75 MHz, CDCl$_3$) δ: 15.2, 17.4, 35.2, 38.2, 42.9, 45.7, 48.0, 50.6, 50.9, 52.1, 53.2, 55.5, 78.2, 91.6, 107.3, 127.7, 132.3, 156.5, 172.9, 177.6; LRMS (m/z): 344 (M$^+$, 15%), 312 (28), 300 (55), 240 (100), 225 (21), 156 (48), 105 (63); HRMS: C$_{20}$H$_{24}$O$_5$ (M$^+$) requires 344.1624, found 344.1620.

Characterization of epi-allogibberic methyl ester: IR (thin film) cm$^{-1}$: 3401br (C—OH), 2930 (C—H), 1732s (C=O), 1435, 1335, 1244, 1158; $^1$H NMR (300 MHz, CDCl$_3$) δ: 1.54-2.20 (m, 7H), 2.24 (s, 3H, —CH$_3$), 2.52 (m, 1H), 2.79 (m, 1H), 3.45 (d, J=8.1 Hz, 1H), 3.66 (s, 3H, —CO$_2$Me), 5.06 (s, 1H), 5.19 (s, 1H), 6.98-7.01 (m, 2H), 7.17 (t, J=7.5 Hz, 1H); $^{13}$C NMR (75 MHz, CDCl$_3$) δ: 18.7, 21.0, 38.3, 38.4, 47.9, 48.8, 51.7, 53.7, 56.2, 78.5, 106.7, 119.8, 127.7, 127.8, 134.8, 139.4, 146.5, 155.4, 172.5. LRMS (m/z): 298 (M$^+$, 42%), 269 (10), 238 (100), 221 (23), 209 (25), 155 (35); HRMS: C$_{19}$H$_{22}$O$_3$ (M$^+$) requires 298.1569, found 298.1567.

Example 3

Synthesis of GA$_5$ Methyl Ester: Solvent Study

A variety of solvents were tested to optimize this aspect of the reaction described in Example 2. Table 1 describes the outcomes of the solvents tested:

TABLE 1

| Solvent | Eq. NaBH$_4$ | Yield or Ratio of GA$_5$ Methyl Ester:epi-Allogibberic Methyl Ester |
| --- | --- | --- |
| DMSO | 5 | A = 68%; B = 12% Ratio: about 7:1 |
| DMSO | 3 | A = 50%; B = 13% Ratio: about 4:1 |
| DMSO | 2 | Ratio: about 4:1 with trace of starting material |
| THF | 3 | Complex mixture |

TABLE 1-continued

| Solvent | Eq. NaBH$_4$ | Yield or Ratio of GA$_5$ Methyl Ester:epi-Allogibberic Methyl Ester |
| --- | --- | --- |
| DMF | 3 | A = 62%; B = 2% with trace of starting material |
| DMF | 3.5 (small scale, 70 mg) | A = 60%; B = 7.2% Ratio: about 10:1 |
| DMF | 3.5 (large scale, 8.4 g) | A = 65%; B = 14% Ratio: about 5:1 |

In general, yields and ratios from experiments carried out in DMF were more reliable and reproducible than those carried out in DMSO.

Example 4

Synthesis of GA$_5$ Alkyl Ester

A variety of GA$_5$ alkyl esters were synthesized to investigate the effect of the alkyl ester on the overall yield of the corresponding GA$_5$ alkyl ester.

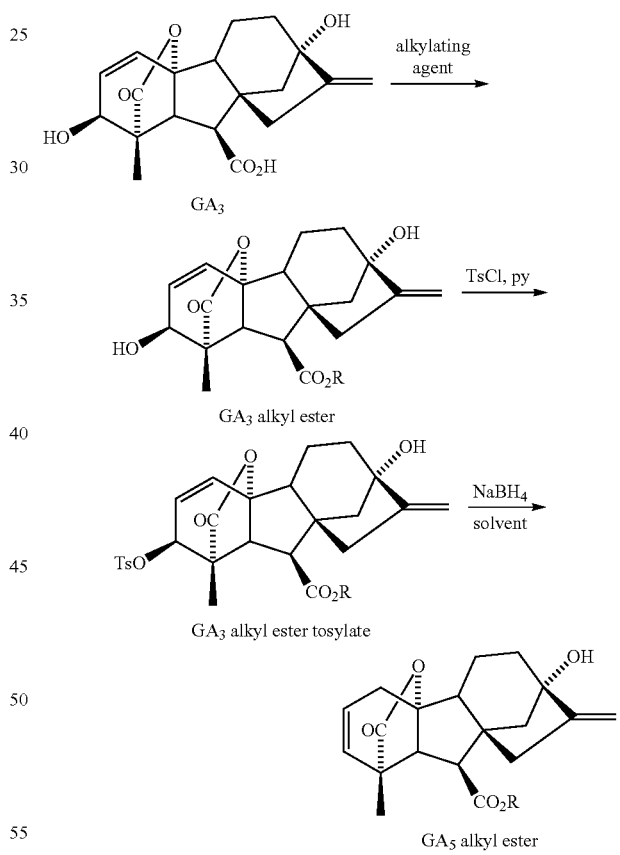

The starting GA$_3$ alkyl ester was prepared by alkylating GA$_3$ using methods well known in the art. For example, the GA$_3$ methyl ester was prepared by alkylating GA$_3$ using methyl iodide and K$_2$CO$_3$. In general, toluenesulfonyl chloride (2.5 equivalents) was added to the purified GA$_3$ alkyl ester (1.0 mmol) in pyridine at 0° C. under nitrogen. After allowing the reaction mixture to stir for 23 hours, methanol (1.50 microliters) was added and the reaction mixture was allowed to stir for an additional 24 hours. The reaction was quenched with water and diluted with chloroform. The organic phase was separated and the aqueous phase was extracted with chloroform, collected, dried with magnesium sulfate and concentrated in vacuo. The resulting $GA_3$ alkyl ester tosylate was purified using silica chromatography. Finally, the $GA_3$ alkyl ester tosylate was converted to the corresponding $GA_5$ alkyl ester using $NaBH_4$.

Table 2 shows the yields of each step for converting the $GA_3$ starting material to the corresponding $GA_5$ alkyl ester.

TABLE 2

| $GA\text{-}CO_2R$ | (percent yield) | | |
|---|---|---|---|
| R = | $GA_3$ alkyl ester | $GA_3$ alkyl ester tosylate | $GA_5$ alkyl ester |
| Methyl | >95 | 80 | 65 |
| Ethyl | 76 | 66 | 49 |
| Benzyl | 77 | 68 | 60 |
| 2-Furyl | 84 | 49 | 49 |

In general, the data reveals that the methyl substituent produces the $GA_5$ alkyl ester in better yields than when an ethyl, benzyl or 2-furyl substituent is used.

* * *

All of the compositions and/or methods disclosed and claimed herein can be made and executed without undue experimentation in light of the present disclosure. While the compositions and methods of this invention have been described in terms of some embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

IV. References

The following references, to the extent that they provide exemplary procedural or other details supplementary to those set forth herein, are specifically incorporated herein by reference.

Great Britain Patent 892777
European Patent 1 094 708
U.S. Pat. No. 5,767,042
U.S. Pat. No. 7,199,082
Bearder et al., *J. Chem. Soc.*, 3:672-8, 1981.
Ben-Tal, *Israel J. of Plant Sciences*, 48:205-215, 2000.
Duri et al., *J. Chem. Soc., Perkins Trans. I*, 1:161-4, 1981.
Greene and Wuts, In: *Protective Groups in Organic Synthesis*, 2nd Ed.; Wiley, NY, 1999.
Grootaert and De Clercq, *Tet. Lett.*, 27:1731-4, 1986.
Hanson, Monograph-British Plant Growth Regulator Group, 5:5-16, 1980.
Joo et al., *Biotech. Lett.*, 26:487-491, 2004.
King and Evans, *Annu. Rev. Plant Biol.*, 54:307-328, 2003.
Longbottom et al., *Angew. Chemie, Int'l Ed.*, 41:2786-2790, 2002.
Longbottom et al., *Tetrahedron*, 59:6955-6966, 2003.
MacMillan et al., *Proc. Chem. Soc.*, 325-6, 1959.
MacMillan et al., *Adv. Chem. Ser.*, 28:18-25, 1961.
Murofushi et al., 41:1075-9, 1977.
Nuyttens et al., *Synlett.*, 7:526-8, 1991.
Pharis, *Planta Berl.*, 105:205-212, 1972.
Pharis and King, *Ann. Review of Plant Physiology*, 36:517-68, 1985.
Shimano et al., *Chem. Pharm. Bull.*, 38:276-8, 1990.
Smith and March, March's Advanced Organic Chemistry: Reactions, Mechanisms, and Structure, 5th ed., Wiley Interscience, New York, 2001.

What is claimed is:

1. A method of preparing a compound of formula (I):

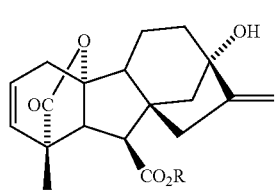

(I)

wherein R is alkyl$_{(C\leq 8)}$, alkenyl$_{(C\leq 8)}$, or aralkyl$_{(C\leq 8)}$, or a substituted version of any of these groups, comprising reacting a compound of formula (II):

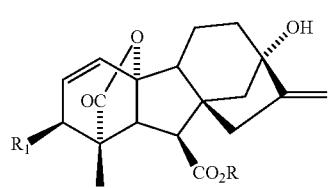

(II)

wherein R is as defined above, and R1 is an alkyl$_{(C\leq 8)}$ sulfonate or an aryl$_{(C\leq 8)}$sulfonate, or a substituted version of either of these groups, in the presence of $NaBH_4$ to produce a mixture comprising the compound of formula (I).

2. The method of claim 1, wherein the reaction of the compound of formula (II) is performed in the presence of a dipolar aprotic solvent.

3. The method of claim 2, wherein the dipolar aprotic solvent is further defined as DMF, DMSO or dimethyl acetamide.

4. The method of claim 1, further comprising obtaining a compound of formula (II).

5. The method of claim 4, wherein the compound of formula (II) is obtained by reacting a compound of formula (III):

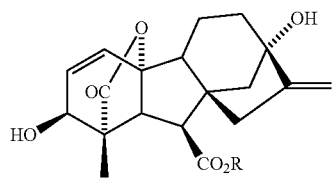

(III)

wherein R is alkyl$_{(C\leq 8)}$, alkenyl$_{(C\leq 8)}$, or aralkyl(C≦8), or a substituted version of any of these groups, in the presence of a sulfonylating agent.

6. The method of claim 5, wherein the sulfonylating agent is an alkyl$_{(C\leq 8)}$sulfonyl chloride or an aryl$_{(C\leq 8)}$sulfonyl chloride.

7. The method of claim 6, wherein the alkyl$_{(C\leq8)}$sulfonyl chloride or the aryl$_{(C\leq8)}$sulfonyl chloride is tosyl chloride, benzenesulfonyl chloride, or methanesulfonyl chloride.

8. The method of claim 1, further comprising isolating the compound of formula (I) from the mixture.

9. The method of claim 1, further comprising removing the R group of the compound of formula (I) to produce GA$_5$.

10. The method of claim 9, wherein the removal is performed before isolation of the compound of formula (I) from the mixture.

11. The method of claim 9, wherein the removal is performed after isolation of the compound of formula (I) from the mixture.

12. The method of claim 1, wherein the number of molar equivalents of NaBH$_4$ ranges from about 1 to about 10.

13. The method of claim 12, wherein the number of molar equivalents of NaBH$_4$ ranges from about 2- to about 5.

14. The method of claim 1, wherein the mixture comprising the compound of formula (I) further comprises a compound of formula (IV):

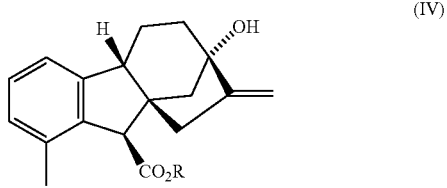

(IV)

wherein R is alkyl$_{(C\leq8)}$, alkenyl$_{(C\leq8)}$, or aralkyl$_{(C\leq8)}$, or a substituted version of any of these groups, and wherein the ratio of the compound of formula (I) to the compound of formula (IV) is greater than 1:1.

15. The method of claim 14, wherein the ratio of the compound of formula (I) to the compound of formula (IV) is greater than about 4:1.

16. The method of claim 14, wherein the ratio of the compound of formula (I) to the compound of formula (IV) is greater than about 7:1.

17. The method of claim 14, wherein the ratio of the compound of formula (I) to the compound of formula (IV) is about 20:1.

18. The method of claim 1, wherein R is alkyl$_{(C\leq8)}$.

19. The method of claim 18, wherein R is methyl.

20. The method of claim 1, wherein R1 is an aryl$_{(C\leq8)}$ sulfonate.

21. The method of claim 20, wherein R1 is tosylate.

22. A method of preparing GA$_5$ comprising:
(a) reacting a compound of formula (II):

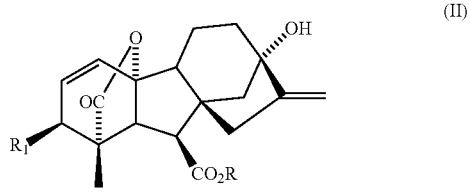

(II)

wherein R is alkyl$_{(C\leq8)}$, alkenyl$_{(C\leq8)}$, or aralkyl$_{(C\leq8)}$, or a substituted version of any of these groups, and R1 is an alkyl$_{(C\leq8)}$sulfonate or an aryl$_{(C\leq8)}$sulfonate, or a substituted version of either of these groups,
in the presence of NaBH$_4$ and a dipolar aprotic solvent to produce a mixture comprising a compound of formula (I):

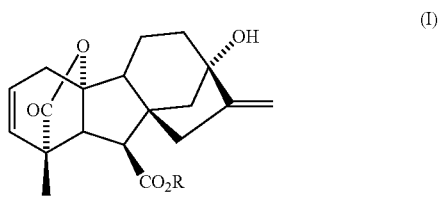

(I)

wherein R is alkyl$_{(C\leq8)}$, alkenyl$_{(C\leq8)}$, or aralkyl$_{(C\leq8)}$, or a substituted version of any of these groups, and
(b) removing the R group of the compound of formula (I) to produce GA$_5$.

23. The method of claim 22, wherein the dipolar aprotic solvent is DMF, DMSO, or dimethyl acetamide.

24. The method of claim 22, further comprising obtaining the compound of formula (II).

25. The method of claim 22, further comprising isolating the compound of formula (I) from the mixture of step (a).

26. The method of claim 22, wherein the removal step of (b) is performed before isolation of the compound of formula (I).

27. The method of claim 22, wherein the removal step of (b) is performed after isolation of the compound of formula (I).

28. The method of claim 22, wherein the number of molar equivalents of NaBH$_4$ ranges from about 1 to about 10.

29. The method of claim 22, wherein the compound of formula (I) is the predominant species in the mixture of step (a).

30. The method of claim 22, wherein the mixture comprising the compound of formula (I) further comprises a compound of formula (IV):

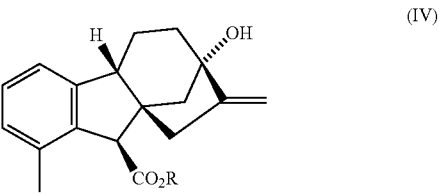

(IV)

wherein R is alkyl$_{(C\leq8)}$, alkenyl$_{(C\leq8)}$, or aralkyl$_{(C\leq8)}$, or a substituted version of any of these groups, and wherein the ratio of the compound of formula (I) to the compound of formula (IV) is greater than 1:1.

31. The method of claim 30, wherein the ratio of the compound of formula (I) to the compound of formula (IV) ranges from about 1:1 to about 20:1.

32. The method of claim 1, wherein R is alkyl$_{(C\leq8)}$.

33. The method of claim 32, wherein R is methyl.

34. The method of claim 1, wherein R1 is an aryl$_{(C\leq8)}$ sulfonate.

35. The method of claim 34, wherein R1 is tosylate.

* * * * *